US010626064B2

(12) United States Patent
Mazoyer et al.

(10) Patent No.: US 10,626,064 B2
(45) Date of Patent: Apr. 21, 2020

(54) PROCESSES TO MAKE NEOPENTANE USING SHELL AND TUBE REACTORS

(71) Applicant: ExxonMobil Chemical Patents Inc., Baytown, TX (US)

(72) Inventors: Etienne Mazoyer, Woluwe Saint Pierre (BE); Kevin B. Daly, Jersey City, NJ (US); Helge Jaensch, Grimbergen (BE); James R. Lattner, La Porte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/390,812

(22) Filed: Apr. 22, 2019

(65) Prior Publication Data

US 2019/0367429 A1 Dec. 5, 2019

Related U.S. Application Data

(60) Provisional application No. 62/677,962, filed on May 30, 2018.

(30) Foreign Application Priority Data

Jun. 14, 2018 (EP) ..................................... 18177656

(51) Int. Cl.
| | | |
|---|---|---|
| *C07C 4/08* | (2006.01) | |
| *C07C 4/10* | (2006.01) | |
| *B01J 23/755* | (2006.01) | |
| *B01J 8/06* | (2006.01) | |
| *B01J 21/08* | (2006.01) | |

(52) U.S. Cl.
CPC ................ *C07C 4/10* (2013.01); *B01J 8/065* (2013.01); *B01J 8/067* (2013.01); *B01J 21/08* (2013.01); *B01J 23/755* (2013.01); *B01J 2208/065* (2013.01)

(58) Field of Classification Search
CPC ...... C07C 2/56; C07C 5/22; C07C 2/06; C07C 4/08
USPC .......................... 585/310, 510, 752, 709, 734
See application file for complete search history.

(56) References Cited

U.S. PATENT DOCUMENTS

| | | | |
|---|---|---|---|
| 2,325,052 | A | 7/1943 | Grosse et al. |
| 2,394,743 | A | 2/1946 | Bergsteinsson |
| 2,413,691 | A | 1/1947 | Crawford et al. |
| 2,422,670 | A | 6/1947 | Haensel et al. |
| 2,422,672 | A | 6/1947 | Haensel et al. |
| 2,422,674 | A | 6/1947 | Haensei et al. |

(Continued)

FOREIGN PATENT DOCUMENTS

| | | |
|---|---|---|
| GB | 574694 | 1/1946 |
| GB | 1220105 | 1/1971 |

(Continued)

OTHER PUBLICATIONS

Vogelzang et al., "Reactions of 2,2-Dimethylbutane on Iridium: The Role of Surface Carbonaceous Layers and Metal Particle Size," Journal of Catalysis, vol. 111, pp. 77-87 (1988).

(Continued)

*Primary Examiner* — Thuan D Dang (57) ABSTRACT

Processes for producing neopentane are disclosed herein. Processes comprise demethylating a $C_6$-$C_8$ alkane within a shell and tube reactor to produce a demethylation product including at least 10 wt % neopentane based on the weight of the demethylation product.

16 Claims, 8 Drawing Sheets

(56) References Cited

U.S. PATENT DOCUMENTS

| | | | |
|---|---|---|---|
| 2,422,675 | A | 6/1947 | Haensel et al. |
| 2,436,923 | A | 3/1948 | Haensel et al. |
| 3,585,252 | A | 6/1971 | Kennedy |
| 3,660,516 | A | 5/1972 | Crain et al. |
| 3,755,493 | A | 8/1973 | Norel |
| 3,855,346 | A | 12/1974 | Norel |
| 4,593,147 | A | 6/1986 | Butter et al. |
| 4,940,829 | A | 7/1990 | Drake |
| 5,146,037 | A | 9/1992 | Zarchy et al. |
| 6,262,192 | B1 | 7/2001 | Wu |
| 2007/0043247 | A1 | 2/2007 | Webber et al. |

FOREIGN PATENT DOCUMENTS

| | | |
|---|---|---|
| WO | 2018/044591 | 3/2018 |
| WO | 2018/044592 | 3/2018 |
| WO | 2018/044596 | 3/2018 |

OTHER PUBLICATIONS

Birkhoff et al., "NExOCTANETM Technology for Isooctane Production," in Handbook of Petroleum Refining Processes, Third Edition, Ch. 1.1 (2004).

Zimmer, H. et al., "Hydrogenolysis of alkanes with quaternary carbon atoms over Pt and Ni black catalysts", J.Chem. Soc., Fararday Trans. 1, 1982.

Himes et al., "UOP HF Alkylation Technology," in Handbook of Petroleum Refining Processes, Third Edition, ch. 1.2 (2004).

Cusher, "UOP Penex Process," Handbook of Petroleum Refining Processes, Third Edition, Ch. 9.3 (2004).

Matsumoto et al., "The classification of metal catalysts in hydrogenolysis of hexane isomers," Journal of Catalysis, vol. 22, pp. 182-192 (1971).

Paál et al, "On the pattern of hydrogenolysis of hexane isomers over four Group VIIIB metals," Reaction Kinetics and Catalysis Letters, vol. 12(2), pp. 131-37 (1979).

Schepers F.J., "Apparent particle size sensitivity in hydrocarbon reactions,"J. Catal, 96, 82-87, 1985.

Richardson J. et al., "Crystallite Size Distributions and Stabilities of Homogeneously Deposited Ni/SiO2 Catalysts," Stu. Sun. Sci. Catal. 3, 131-142, 1979.

Song C. et al., "Properties of the Ni/Kieselguhr catalysts prepared by precipitation method," Korean J. of Chem. Eng. 9 (3) 159-163, 1992.

Zidek, Zdeno et al., "Nickel-silica-alumina catalysts. III. Catalytic properties. Hydrocracking of isooctane", 1969.

Seth et al., "Selective hydrogenation of 1,3-butadiene in mixture with isobutene on a Pd/@a-alumina catalyst in a semi-batch reactor", vol. 62, No. 17.

Avdonina, E.N., "Reactions of tritium recoil atoms in liquid mixtures of isooctane with benzene," XP002768312 & vol. 15, No. 5, 1973, pp. 720-726.

Clarke et al., "The Preparation and Activity for Alkane Reactions of Aerosil-Supported Rhodium-Copper Clusters," Journal of Catalysis, vol. 111, pp. 374-382 (1988).

Haensel et al., "Selective Demethylation of Paraffin Hydrocarbons: Preparation of Triptane and Neopentane," Industrial and Engineering Chemistry, vol. 39, pp. 853-857 (1947).

Foger et al., "Skeletal Reactions of Hydrocarbons over Supported Iridium-Gold Catalysts," Journal of Catalysis, vol. 64, pp. 448-463 (1980).

Machiels, et al., "Hydrogenolysis of 2, 2-Dimethylbutane and n-Hexane over Supported Ruthenium, Nickel, Cobalt, and Iron," Journal of Catalysis, vol. 58, pp. 268-275 (1979).

Leclercq et al., "Hydrogenolysis of Saturated Hydrocarbons: Influence of Hydrocarbon Structures on the Activity and Selectivity of Nickel on Silica," Journal of Catalysis, vol. 99, pp. 1-11.

Kranz, K., "Alkylation chemistry-Mechanism, operating variables, and olefin interactions", DuPont Company, 2003.

Graves, "STRATCO Effluent Refrigerated H2SO4 Alkylation Process," in Handbook of Petroleum Refining Processes, Third Edition, ch. 1.2 (2004).

Roeseler, "UOP AlkyleneTM Process for Motor Fuel," in Handbook of Petroleum Refining Processes, Third Edition, ch. 1.3 (2004).

Matsumoto et al., "Contrast between nickel and platinum catalysts in hydrogenolysis of saturated hydrocarbons," Journal of Catalysis, vol. 19(2), p. 101 (1970).

Richardson J. et al , "Preparation variables in nickel catalysts", J. Catal. 54, 207-218, 1978.

Mendioroz S. et al., "Effect of the method of preparation on the activity of nickel Kieselguhr catalyst for vegetable oil hydrogenation," Appl. Catal. 66, 73-90, 1990.

Hadley, G.R., "Thermal conductivity of packed metal powders," International Journal of Heat and Mass Transfer 29.6, 909-920, 1986.

Coenen J., "Catalytic hydrogenation of fatty oils," Ind. Eng. Chem. Fundamen. 25 (1) 43-52, 1986.

Ponec et al., "Reaction of hexane isomers on Ni-Copper alloys," Proceedings of the Fifth International Congress on Catalysis, p. 645 (1972).

Bergman et al., Fundamentals of Heat and Mass Transfer, John Wiley & Sons.

PROCESSES TO MAKE NEOPENTANE USING SHELL AND TUBE REACTORS

CROSS-REFERENCE TO RELATED APPLICATIONS

This application claims the benefit of Provisional Application No. 62/677,962, filed May 30, 2018 and European Application No. 18177656.8, filed Jun. 14, 2018. This disclosure is related to WO 2018/044591, filed Aug. 18, 2017, WO 2018/044592, filed Aug. 18, 2017, and WO 2018/044596, filed Aug. 18, 2017, each of which is incorporated herein by reference in their entireties.

FIELD OF INVENTION

The present invention relates to methods of producing neopentane and uses thereof.

BACKGROUND OF INVENTION

Neopentane is a unique nonpolar hydrocarbon molecule that has found industrial use in the form of an inert condensing agent for gas-phase reactions. See, for instance, U.S. Pat. No. 6,262,192. Other potential industrial uses for neopentane include use as a heat removal agent, a blowing agent, and a gasoline blend component due to its relatively high octane numbers. For instance, neopentane has a Research Octane Number (RON) of 85.5 and a Motor Octane Number (MON) of 80.2.

Many conventional processes for producing neopentane have proven unsatisfactory for application on a commercial scale. For example, typical existing processes for synthesizing neopentane utilize stoichiometric reactions of t-butyl-chloride and a Grignard reagent, methyl aluminum dichloride, dimethyl aluminum chloride, or trimethyl aluminum. See, for instance, U.S. Pat. No. 3,585,252. Such stoichiometric reactions generate large amounts of metal halides and are difficult to scale up to produce neopentane at commercial quantities. Likewise, though neopentane may be synthesized by hydrogenation of neopentanoic acid under high pressure and at high temperature, e.g., as described in U.S. Pat. No. 4,593,147, such processes are expensive due to the neopentanoic acid feedstock and suffer from a combination of demanding reaction conditions and low selectivity.

Other proposed processes for producing neopentane involve demethylation of higher carbon-number branched paraffins. For example, U.S. Pat. Nos. 4,940,829 and 2,422,675 each relate to the preparation of neopentane via catalytic demethylation of neohexane. However, these higher carbon-number branched paraffins are not readily available in high concentrations suitable as feedstock that could be utilized on a commercial scale.

Alternatively, a process for producing neopentane by hydrogenating an isobutylene polymer and selectively cracking the hydrogenation product is described in U.S. Pat. No. 2,394,743. However, in addition to producing neopentane, this process also produces large amounts of heavier hydrocarbon components.

The production of neopentane by processes that include the demethylation of higher carbon-number hydrocarbons have recently be disclosed in related applications. For instance, WO 2018/044591 discloses a process that includes dimerizing isobutylene to produce diisobutylene, hydrogenating the diisobutylene to yield isooctane, and demethylating the diisobutylene to produce neopentane. Further, WO 2018/044592 discloses a process that includes isomerizing C6 and/or C7 paraffins to produce neohexane and/or neoheptane and demethylating the neohexane and/or neoheptane to produce neopentane. Further still, WO 2018/044596 discloses a process that includes contacting isobutane and butylene under alkylation conditions to produce isooctane and demethylating the isooctane to produce neopentane. Each of these processes is reliant upon a suitable catalyst for the demethylation of the higher carbon-number hydrocarbons to produce neopentane. However, demethylation of the higher carbon-number hydrocarbons to produce neopentane is highly exothermic.

Thus, there is a need for temperature control of the demethylation process used to produce neopentane. Effective temperature control of the demethylation of the higher carbon-number hydrocarbons would allow processes such that those described above to more economically produce neopentane in commercial quantities.

Other references of interest include: "The Preparation and Activity for Alkane Reactions of Aerosil-Supported Rhodium-Copper Clusters," Clarke et al., *Journal of Catalysis*, vol. 111, pp. 374-82 (1988); "Selective Demethylation of Paraffin Hydrocarbons: Preparation of Triptane and Neopentane," Haensel et al., *Industrial and Engineering Chemistry*, vol. 39, pp. 853-57 (1947); "Skeletal Reactions of Hydrocarbons over Supported Iridium-Gold Catalysts," Foger et al., *Journal of Catalysis*, vol. 64, pp. 448-63 (1980); "Reactions of 2,2-Dimethylbutane on Iridium: The Role of Surface Carbonaceous Layers and Metal Particle Size," Vogelzang et al., *Journal of Catalysis*, vol. 111, pp. 77-87 (1988); "Hydrogenolysis of 2,2-Dimethylbutane and n-Hexane over Supported Ruthenium, Nickel, Cobalt, and Iron," Machiels et al., *Journal of Catalysis*, vol. 58, pp. 268-75 (1979); "Hydrogenolysis of Saturated Hydrocarbons: Influence of Hydrocarbon Structures on the Activity and Selectivity of Nickel on Silica," Leclercq et al., *Journal of Catalysis*, vol. 99, pp. 1-11; GB 574694; U.S. Pat. Nos. 2,422,670; 2,436,923; "STRATCO Effluent Refrigerated $H_2SO_4$ Alkylation Process," in Handbook of Petroleum Refining Processes, Third Edition, Graves, ch. 1.2 (2004); and "UOP Alkylene™ Process for Motor Fuel," in Handbook of Petroleum Refining Processes, Third Edition, Roeseler, ch. 1.3 (2004); and "UOP HF Alkylation Technology," in Handbook of Petroleum Refining Processes, Third Edition, Himes et al., ch. 1.2 (2004).

SUMMARY OF THE INVENTION

Described herein are processes and systems for producing neopentane that address the need for temperature control in the production of neopentane by demethylation of higher carbon-number alkanes. The processes include demethylating a $C_6$-$C_8$ alkane within a shell and tube reactor to produce a demethylation product including neopentane. Typically, the shell and tube reactor includes at least one tube, preferably a plurality of tubes, having a diameter from 10 mm to 100 mm, preferably from 40 mm to 60 mm.

Described is a process for producing neopentane, the process comprising (or consisting of, or consisting essentially of) demethylating a $C_6$-$C_8$ alkane within a shell and tube reactor to produce a demethylation product including at least 10 wt % neopentane based on the weight of the demethylation product.

DETAILED DESCRIPTION OF THE EMBODIMENTS

Definitions

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, for example, embodiments using "a fractionation column" include embodiments where one, two or more fractionation columns are used, unless specified to the contrary or the context clearly indicates that only one fractionation column is used. Likewise, "a $C_{12}$+ component" should be interpreted to include one, two or more $C_{12}$+ components unless specified or indicated by the context to mean only one specific $C_{12}$+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, for example, the concentrations of the various components of a stream are expressed based on the total weight of that stream. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, "hydrocarbon" refers to molecules or segments of molecules containing primarily hydrogen and carbon atoms. As used herein, the term "$C_n$" hydrocarbon wherein n is a positive integer, e.g., 1, 2, 3, 4, etc., means a hydrocarbon having n number of carbon atom(s) per molecule. The term "$C_n$+" hydrocarbon wherein n is a positive integer, e.g., 1, 2, 3, 4, etc., as used herein, means a hydrocarbon having at least n number of carbon atom(s) per molecule. The term "$C_n$–" hydrocarbon wherein n is a positive integer, e.g., 1, 2, 3, 4, etc., used herein, means a hydrocarbon having no more than n number of carbon atom(s) per molecule.

As used herein, "olefin" refers to any unsaturated hydrocarbon having the formula $C_nH_{2n}$ and containing one carbon-carbon double bond, wherein C is a carbon atom, H is a hydrogen atom, and n is the number of carbon atoms in the olefin.

As used herein, "alkane" or "paraffin" refers to any saturated hydrocarbon having the formula $C_nH_{2n+2}$, wherein C is a carbon atom, H is a hydrogen atom, and n is the number of carbon atoms in the alkane.

As used herein, a "primary carbon atom" refers to a carbon atom neighboring one carbon atom, "secondary carbon atom" refers to a carbon atom neighboring two carbon atoms, "tertiary carbon atom" refers to a carbon atom neighboring three carbon atoms, and "quaternary carbon atom" refers to a carbon atom neighboring four carbon atoms.

As used herein, the prefix "normal" or "n-" signifies a linear unbranched hydrocarbon.

As used herein, the prefix "iso" or "i-" signifies a hydrocarbon containing a methyl substitution at the second carbon of the hydrocarbon chain.

As used herein, the prefix "neo" signifies a hydrocarbon containing a quaternary carbon atom. For example, the term "neopentane" refers to a compound of the formula $C_5H_{12}$ and containing a quaternary carbon atom, otherwise known as 2,2-dimethylpropane.

$C_6$-$C_8$ Alkanes

In any embodiment, the $C_6$-$C_8$ alkane which can be demethylated to produce neopentane can be neohexane (2,2-dimethylbutane), neoheptane (2,2-dimethylpentane), or isooctane (2,2,4-trimethylpentane). The neohexane, neoheptane, and/or isooctane can be can be prepared by any suitable method. For example, isobutylene can be dimerized to produce diisobutylene and the diisobutylene can be hydrogenated to yield isooctane, as disclosed in WO 2018/044591:

Additionally or alternatively, $C_6$ and/or $C_7$ paraffins can be isomerized to produce neohexane and/or neoheptane, as disclosed in WO 2018/044592. Additionally or alternatively, isobutane and butylene can be contacted under alkylation conditions to produce isooctane, as disclosed in WO 2018/044596.

Demethylation of the $C_6$-$C_8$ Alkane

In any embodiment, demethylating a $C_6$-$C_8$ alkane may comprise contacting a stream comprising the $C_6$-$C_8$ alkane with hydrogen in the presence of a catalyst within a shell and tube reactor. Typically, the shell and tube reactor includes one or more tubes, which may collectively be referred to as a tube bundle, defining one of more reaction zones. The shell and tube reactor can include an inlet plenum (e.g., an inlet manifold) configured to receive the reactants (e.g., a stream including the $C_6$-$C_8$ alkane and a hydrogen stream) and to distribute the reactants to the tube bundle. The shell and tube reactor can also include an outlet plenum configured to receive the products of the demethylation reaction. The shell and tube reactor may have any suitable configuration, examples of which include a single-pass, straight-tube configuration; a multi-pass, straight-tube configuration; or a U-tube configuration.

In any embodiment, the tubes of the shell and tube reactor may have an internal or outside diameter of 10 mm to 100 mm, preferably 20 mm to 80 mm, more preferably 30 mm to 70 mm, and most preferably 40 mm to 60 mm. The tubes can have a suitable cross-sectional flow-area of about 80 $mm^2$ to about 30,000 $mm^2$, or about 300 $mm^2$ to about 5,000 $mm^2$, or about 1,250 $mm^2$ to about 3,000 $mm^2$. The tubes can also have a suitable cross-sectional shape, for example, the tubes can be circular, elliptical, oblong, rectangular, square, polygonal, or any suitable combination thereof. Additionally, in any embodiment, the tube walls may have a heat transfer coefficient of about 400 $W/m^2/K$ to about 800 $W/m^2/K$, or about 500 $W/m^2/K$ to about 750 $W/m^2/K$, or about 600 $W/m^2/K$ to about 700 $W/m^2/K$.

In any embodiment, at least a portion of each of the tubes is disposed within an internal volume defined by a shell. The shell may include an inlet for conveying a heat-exchange fluid into the internal volume of the shell and an outlet for conveying the heat-exchange fluid out of the internal volume of the shell. The internal volume can include one or more baffles to direct fluid movement through the shell.

Additionally, it may be desirable to maximize the volume fraction occupied by the tubes inside the reactor shell, as this may keep the total reactor size to a minimum. Volume fraction can depend upon the amount of space between tubes and the tube diameter. Therefore, in any embodiment, a minimum of 5 mm or a minimum of 6 mm space between tubes may be present. For example, when the outside diameter of the tubes is about 50 mm, and with triangular spacing and a 6 mm gap between tubes, the volume faction occupied by the tubes (based on outside diameter) is about 72%. Therefore, in any embodiment, the volume fraction can be greater than 30%, greater than 35%, greater than 40%, greater than 45%, greater than 50%, greater than 55%, and preferably greater than 60%, with a tube spacing no less than 5 mm.

The reaction pathway for the conversion of the $C_6$-$C_8$ alkanes to neopentane typically proceeds by a step-wise demethylation from isooctane to neoheptane, from neoheptane to neohexane, and from neohexane to neopentane, as summarized in the following reaction schemes:

-continued

As shown from the reaction scheme above, the desired demethylation occurs at the tertiary (3°) carbon of the isooctane and the secondary (2°) carbon of the intermediates. Competing demethylation reactions can occur at the quaternary (4°) carbon. Advantageously, the catalysts used in the demethylation are effective to minimize demethylation at the quaternary (4°) carbon to prevent a loss of neopentane yield.

In any embodiment, the overall conversion of $C_6$-$C_8$ alkane during the demethylation step can be greater than 50%, greater than 80%, greater than 95%, and preferably greater than 99%. Additionally or alternatively, the overall conversion of $C_6$-$C_8$ alkane can be about 80% to about 99% or about 90% to about 99%.

The product of the demethylation step generally comprises neopentane, $C_4$- hydrocarbon components (e.g., methane, ethane, and propane) and, optionally, partially converted $C_6$+ hydrocarbon intermediate components (e.g., neohexane and neoheptane). Preferably, the product of the demethylation step comprises: at least 10 wt %, preferably at least about 25 wt %, preferably at least about 35 wt %, and ideally at least about 50 wt % of neopentane, such as about 25 wt % to about 50 wt % or about 30 wt % to about 40 wt %; less than about 75 wt %, preferably less than about 65 wt %, and preferably less than about 50 wt % of $C_4$- hydrocarbon components such as about 25 wt % to about 75 wt % or about 40 wt % to about 60 wt %; less than about 5 wt %, preferably less than about 1 wt %, and ideally less than about 0.5 wt % of non-neopentane $C_5$ hydrocarbon components, such as about zero wt % to about 1 wt %; and less than about 10 wt %, preferably less than about 5 wt %, preferably less than about 1 wt %, and ideally less than about 0.5 wt % of partially converted $C_6$+ hydrocarbon components (e.g., $C_6$-$C_7$ hydrocarbons), such as about zero wt % to about 10 wt %, or about zero wt % to about 1 wt %, or about 0.5 wt % to about 1 wt %.

In any embodiment, the light $C_4$- hydrocarbon components and the $C_6$+ hydrocarbon intermediate components can be removed from the demethylation product, for example, by distillation, thereby yielding a purified neopentane product stream. Preferably, the purified neopentane product stream comprises greater than about 80 wt % neopentane, or greater than about 90 wt % neopentane, or greater than about 95 wt % neopentane, or greater than about 99 wt % neopentane, such as about 80 wt % to about 99 wt % neopentane, or about 85 wt % to about 95 wt % neopentane when starting with a $C_6$ alkane feed. Other feeds may depend upon the process, for example per pass conversion may be limited to 20% with a recycling loop.

In any embodiment, demethylating the $C_6$-$C_8$ alkane can be conducted at a temperature of about 200° C. to about 500° C., or about 300° C. to about 400° C. and a pressure at about 100 kPa absolute to about 10000 kPa absolute (e.g., atmospheric to about 1500 psia), such as about 300 kPa absolute to about 8000 kPa absolute, in the presence of the catalyst. Often demethylation can be conducted at a hydrogen partial pressure of about 50 kPa absolute to about 3500 kPa absolute (e.g., from about 7 psia to about 500 psia). Typically, demethylation can be conducted at a hydrogen partial pressure of less than about 2500 kPa absolute, preferably less than about 2200 kPa absolute, and preferably less than about 1000 kPa absolute (e.g., preferably less than about 350 psia, or preferably less than about 150 psia). Additionally or alternatively, demethylation can be conducted at a hydrogen to hydrocarbon molar ratio of about 2:5 to about 25:1, or about 1:2 to about 20:1, or about 1:1 to about 14:1. In further embodiments, demethylation may be conducted under conditions including a temperature from about 220° C. to about 300° C.; a pressure from about 15 psig to about 200 psig (e.g., from about 205 kPa absolute to about 1400 kPa absolute); and a hydrogen to hydrocarbon molar ratio of about 1:1 to about 14:1; or any combination thereof.

Generally, the catalyst employed in the demethylation comprises a transition metal component. Non-limiting examples of suitable transition metal components include Fe, Co, Ni, Rh, Ir, Ru, Pt, and Pd, a combination thereof, a compound thereof, and a mixture of compounds thereof, with Ni being particularly advantageous. Often, the transition metal component contains transition metal as a single component. Alternatively, the transition metal component may contain a transition metal combined with one or more additional metals to form a binary or ternary alloy. Non-limiting examples of suitable additional metals include Cu, Au, Ag, Sn, Zn, Re, a combination thereof, a compound thereof, and a mixture of compounds thereof. Desirably, the amount of the transition metal component present in the catalyst is about 0.05 wt % to about 60.0 wt %, such as about 0.10 wt % to about 50.0 wt %, based on the total weight of the catalyst. Generally, the transition metal component is to supported on a non-acidic support material. Non-limiting examples of suitable support materials include silica, theta-alumina, clay, pentasil, aluminophosphate, carbon, titania, zirconia, and a mixture thereof. Examples of catalysts that may be used in the processes described herein include: nickel supported on silica, cobalt on silica, nickel on alumina, platinum on silica, and palladium on silica.

Preferably, the acidity of the catalyst employed in the demethylation is minimized to inhibit undesired cracking reactions. Often, the acidity of the catalyst is reduced via impregnation with an alkali metal compound, preferably an alkali metal hydroxide, nitrate, carbonate, bicarbonate, or oxide, such as sodium oxide, e.g., $Na_2O$. Desirably, the amount of the alkali metal compound present in the catalyst is from about 0.05 wt % to about 1.0 wt %, such as from about 0.1 wt % to about 0.5 wt %, of the total weight of the catalyst.

Process

The processes and systems described herein will now be more particularly described with reference to FIG. 1, FIG. 2, FIG. 3, and FIG. 4.

Figure 1:
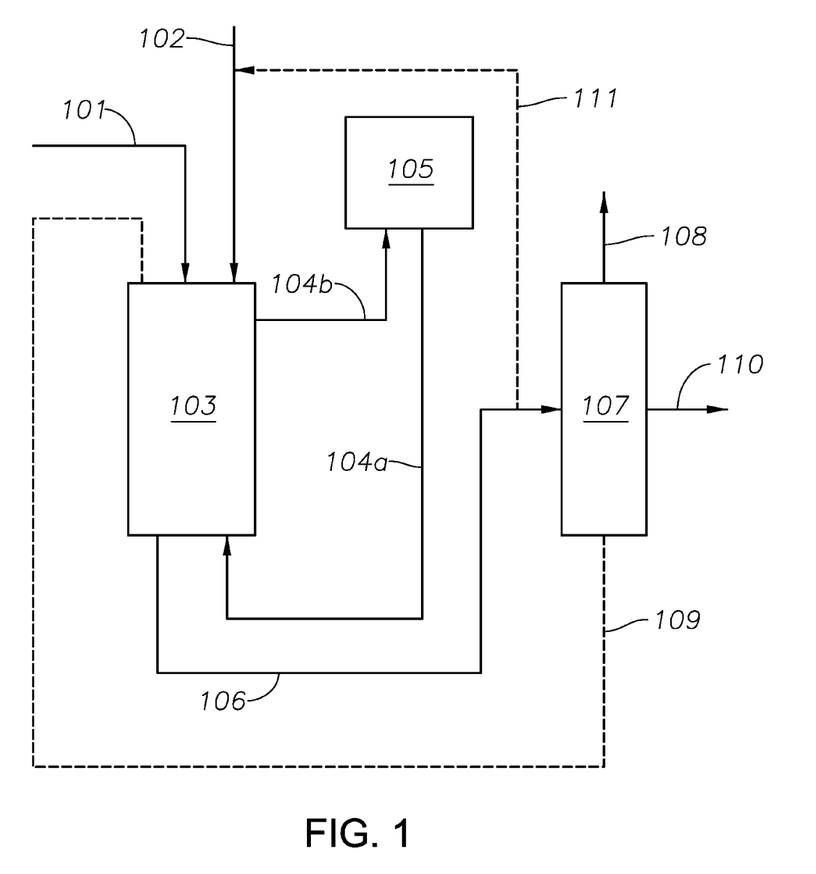
FIG. 1 is a diagram of an example process of making neopentane as described herein.

FIG. 1 illustrates an example neopentane production process described herein, in which a $C_6$-$C_8$ alkane is demethylated to yield neopentane. As shown in FIG. 1, a feed stream 101 comprising the $C_6$-$C_8$ alkane and a hydrogen stream 102 are introduced to a shell and tube reactor 103. The feed stream 101 and the hydrogen stream 102 are shown separately entering the shell and tube reactor 103, however the feed stream 101 and hydrogen stream 102 may enter the shell and tube reactor 103 through the same inlet (not shown). The shell and tube reactor 103 can also receive a heat-exchange fluid 104a, for example, water. At least a portion of the heat-exchange fluid 104a can optionally leave the shell and tube reactor as spent heat-exchange fluid 104b and cycle through a waste-heat recovery unit 105 where it can be cooled again. The demethylation reaction yields a demethylation effluent 106 comprising neopentane, $C_4$- hydrocarbons, and partially converted components, e.g., $C_6$+ hydrocarbons. The demethylation effluent 106 can then be fed to a separator 107, for example, a distillation column, to separate a light fraction 108 comprising $C_4$- hydrocarbons and a heavy fraction 109 comprising partially converted $C_6$+ hydrocarbons (primarily, $C_6$-$C_7$ hydrocarbons) from the demethylation effluent 106. The resulting obtained fraction 110 is mainly composed of neopentane. The light fraction 108 can be subjected to further downstream treatment for use as fuel. Optionally, at least a portion of the heavy fraction 109 can be recycled to the shell and tube reactor 103. Also, optionally, at least a portion of unreacted hydrogen 111 can be separated from the demethylation effluent 106 and recycled to the shell and tube reactor 103. Any suitable means can be used to separate unreacted to hydrogen 111 from the demethylation effluent 106, such as a splitter, distillation or suitable membrane.

Figure 2:
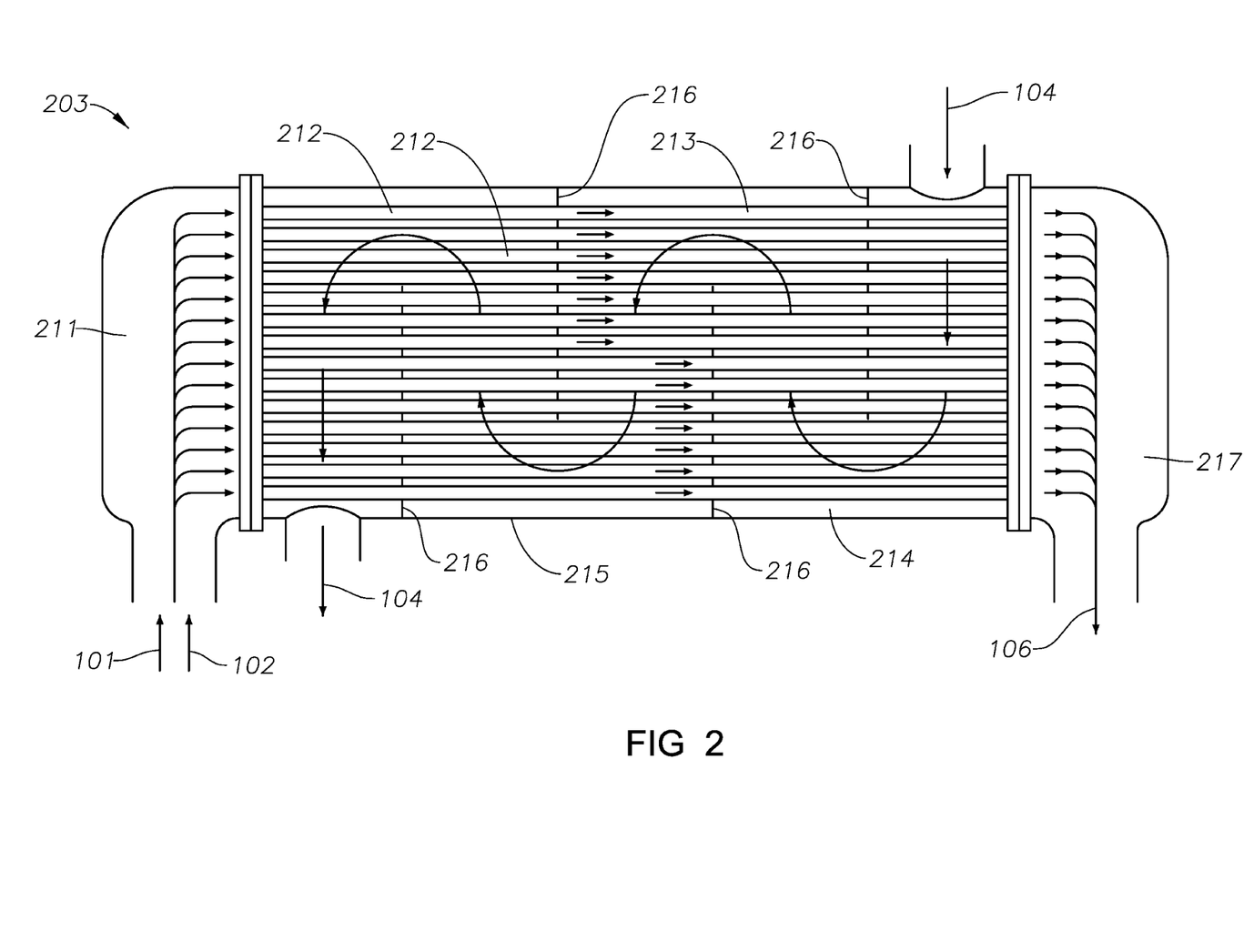
FIG. 2 is an example shell and tube reactor as described herein.

FIG. 2 illustrates an example of shell and tube reactor 203. In FIG. 2, the shell and tube reactor 203 has a straight-tube, one pass configuration. The feed stream 101 comprising the $C_6$-$C_8$ alkane and the hydrogen stream 102 are introduced into an inlet plenum 211 and pass through tubes 212 defining a reaction zone 213. The tubes 212 are disposed within an internal volume 214 defined by a shell 215 and are surrounded by the heat-exchange fluid 104. In FIG. 2, the tubes 212 are straight and pass through the internal volume 214 in only a single direction (e.g., the straight-tube, one pass configuration). The internal volume 214 includes baffles 216 configured to direct the movement of the heat-exchange fluid 104 through the internal volume 214, for example, so as to maximize heat-exchange between the tubes 212 and the heat-exchange fluid 104. The demethylation effluent 106 exits the shell and tube reactor 203 via an outlet plenum 217.

Figure 3:
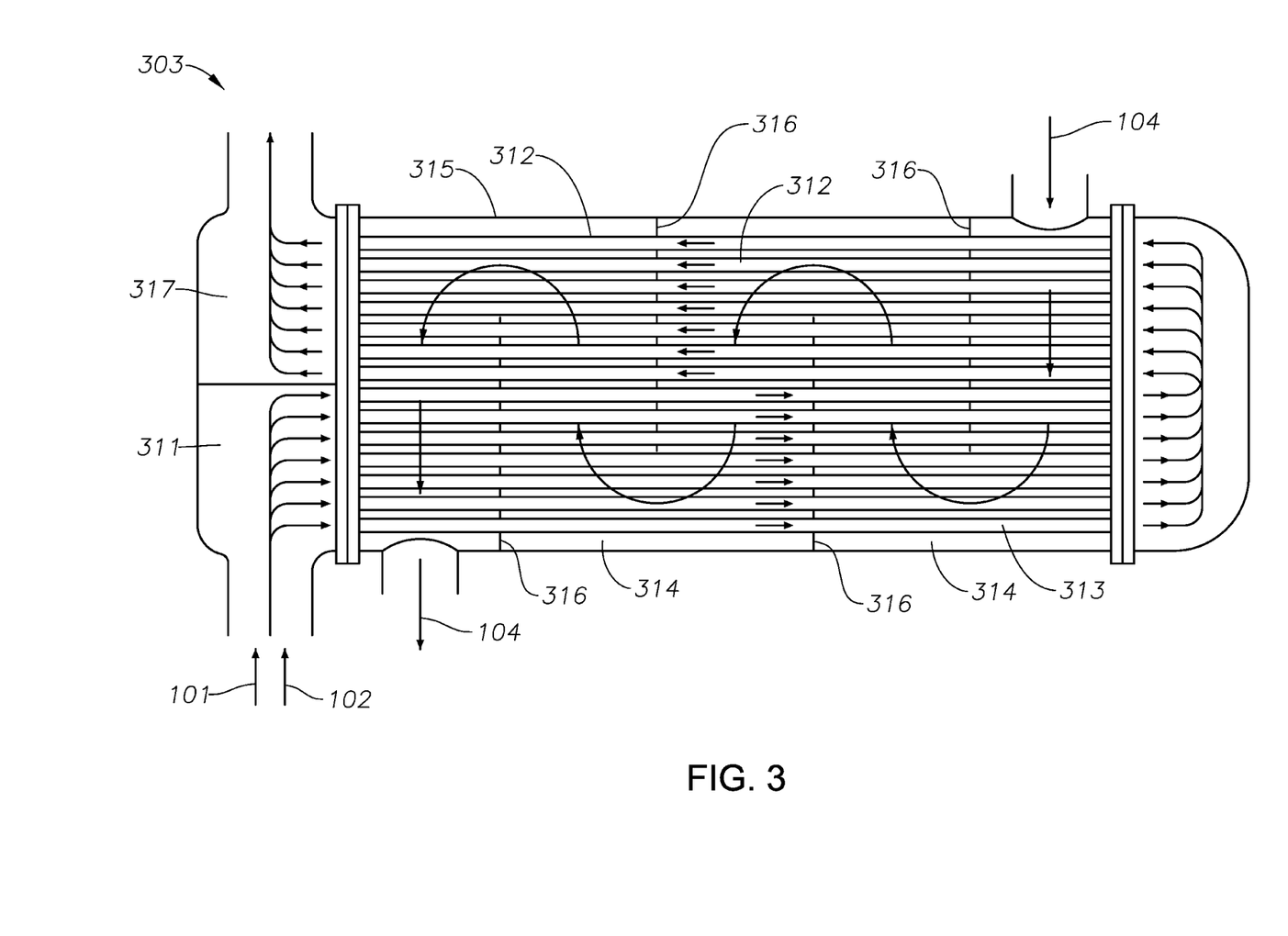
FIG. 3 is an example of another shell and tube reactor as described herein.

FIG. 3 illustrates another example of a shell and tube reactor 303. In FIG. 3, the shell and tube reactor 303 has a straight-tube, multi-pass configuration as opposed to the one pass configuration example of FIG. 2. The feed stream 101 comprising the $C_6$-$C_8$ alkane and the hydrogen stream 102 are introduced into an inlet plenum 311 and pass through tubes 312 defining a reaction zone 313. The tubes 312 are disposed within an internal volume 314 defined by a shell 315 and are surrounded by the heat-exchange fluid 104. In FIG. 3, the tubes 312 are straight and pass through the internal volume 314 in two directions (e.g., the straight-tube, multi-pass configuration). For example, flow can be through a first portion of the tubes 312 is in a first direction and flow can be through a second portion of the tubes 312 is in a second direction, opposite to the first. The internal volume 314 includes baffles 316 configured to direct the movement of the heat-exchange fluid 104 through the internal volume 314, for example, so as to maximize heat-exchange between the tubes 312 and the heat-exchange fluid 104. The demethylation effluent 106 exits the shell and tube reactor 303 via an outlet plenum 317.

Figure 4:
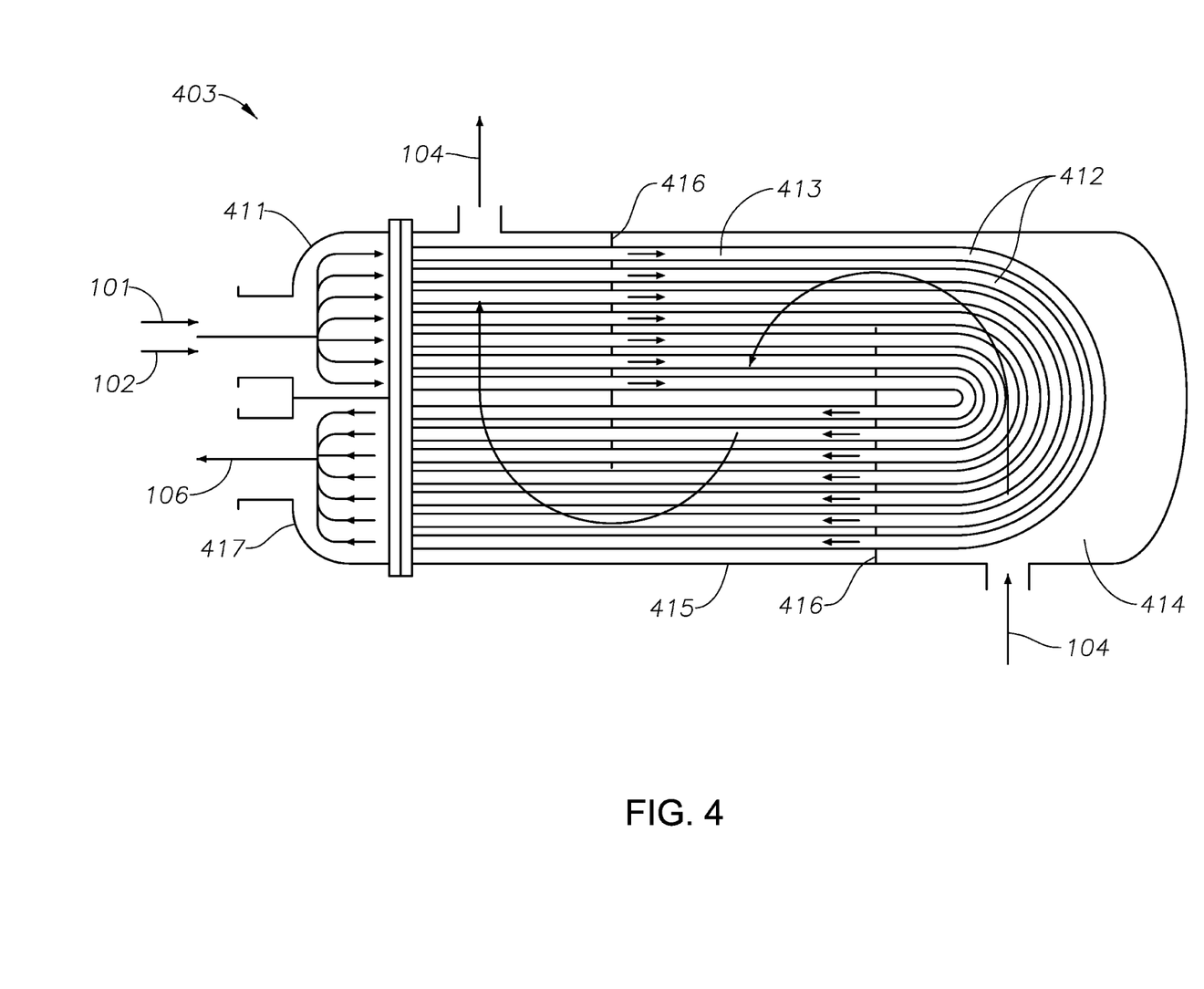
FIG. 4 is an example of another shell and tube reactor as described herein.

FIG. 4 illustrates another example of a shell and tube reactor 403. In FIG. 4, the shell and tube reactor 403 has a U-tube configuration. The feed stream 101 comprising the $C_6$-$C_8$ alkane and the hydrogen stream 102 are introduced into an inlet plenum 411 and pass through tubes 412 defining a reaction zone 413. The tubes 412 are disposed within an internal volume 414 defined by a shell 415 and are surrounded by the heat-exchange fluid 104. In FIG. 4, the tubes 412 are U-shaped. The internal volume 414 includes baffles 416 configured to direct the movement of the heat-exchange fluid 104 through the internal volume 414, for example, so as to maximize heat-exchange between the tubes 412 and the heat-exchange fluid.

Neopentane produced in accordance with the present invention is useful as a blowing agent for the production of foamed polymers and possesses several properties (e.g., a boiling point of 9.5° C. and a freezing point of −16.6° C.) making it useful as a heat removal agent and/or an inert condensing agent (ICA) in gas phase polymerization process, such as gas phase polymerization processes for the production of polyethylene. Neopentane produced in accordance with this invention also exhibits high octane numbers and is therefore useful as a gasoline blend component.

The invention will now be more particularly described with reference to the accompanying drawings and the following non-limiting Examples.

EXAMPLE

The following prophetic example demonstrates a shell and tube reactor having design parameters that allow for adequate heat removal in order to control the demethylation of $C_6$-$C_8$ alkanes to neopentane. Table 1 demonstrates the adiabatic temperature rises modeled with respect to various $H_2$:HC ratios, for isooctane to neopentane, isooctane to pentane, neohexane to neopentane, and neohexane to methane:

TABLE 1

Modeled Temperature Rise

| $H_2$:HC Ratio [mol:mol] | iC8 to neoC5 [° C.] | iC8 to $CH_4$ [° C.] | neoC6 to neoC5 [° C.] | neoC6 to $CH_4$ [° C.] |
|---|---|---|---|---|
| 1 | 168.0 | 160.6 | 215.2 | 230.0 |
| 2 | 304.8 | 292.6 | 196.0 | 360.7 |
| 3 | 420.4 | 405.1 | 179.8 | 491.3 |
| 4 | 396.6 | 503.5 | 165.9 | 603.1 |
| 5 | 375.1 | 590.8 | 154.0 | 700.7 |
| 6 | 355.6 | 669.3 | 143.6 | 659.7 |
| 7 | 337.9 | 740.4 | 134.4 | 622.8 |
| 8 | 321.7 | 707.9 | 126.3 | 589.4 |
| 9 | 306.9 | 677.9 | 119.1 | 559.2 |
| 10 | 293.3 | 650.1 | 112.7 | 531.6 |
| 11 | 280.8 | 624.3 | 106.9 | 506.4 |
| 12 | 269.2 | 600.3 | 101.6 | 483.3 |
| 13 | 258.5 | 577.9 | 96.8 | 462.1 |
| 14 | 248.6 | 556.9 | 92.5 | 442.5 |
| 15 | 239.3 | 537.4 | 88.5 | 424.4 |
| 16 | 230.7 | 519.0 | 84.8 | 407.6 |
| 17 | 222.7 | 501.7 | 81.5 | 392.0 |

Due to the highly exothermic nature of the reaction of $C_6$-$C_8$ alkanes to neopentane, as shown in Table 1, the reaction should be controlled and the possibility of a runaway reaction should be mitigated. The design parameters for a shell and tube reactor modeled below demonstrate that these parameters are effective to remove sufficient heat in order to maintain a safe, steady-state temperature profile.

The key inputs relied upon in this model include reaction rate laws, fouling to resistances at the walls, and effective bed thermal conductivity. In order to simplify the development of the model, the following assumptions were made:
the reactor is sized for no axial temperature rise at steady state;
there is negligible mass diffusion/dispersion and, thus, bulk convection will dominate over mass diffusion/dispersion;
the pressure throughout the reactor is substantially uniform, for example, a total pressure more than 150 psig is large relative to a reactor pressure drop of about 5 psi;
there is negligible cooling from axial convection and/or dispersion;
the shell-side temperature is substantially constant. In this example, the heat exchange fluid is water, and most of the cooling is via latent heat, as opposed to specific heat;
the shell-side has liquid-phase transport properties; and
the heat of reaction (W/m³) at a given axial coordinate and radial coordinate equals the heat release where the radial coordinate is equal to 0. This is a conservative approximation, since the temperature, and therefore the heat release, are highest where the radial coordinate is equal to 0.

Based upon these assumptions, the steady-state energy balance and boundary conditions at a given axial coordinate can be reduced to the equations that follow:

$$\frac{1}{r}\frac{d}{dr}\left(r\frac{dT}{dr}\right) + \frac{\dot{q}(T)}{k} = 0; \quad \text{Eq. (1)}$$

$$\left.\frac{dT}{dr}\right|_{r=0} = 0; \quad \text{Eq. (2)}$$

$$T(r = R) = T_S; \quad \text{Eq. (3)}$$

$$T_S = T_\infty + \frac{\dot{q}dot(Tmax)}{2h}; \text{ and} \quad \text{Eq. (4)}$$

$$\dot{q}(T) = \Delta H_{rxn} A \exp\left(-\frac{E_a}{R_g T}\right)\frac{p_{HC}^\alpha}{p_{H_2}^\beta}, \quad \text{Eq. (5)}$$

where:
T Bed temperature;
r Radial coordinate;
z Axial coordinate;
k Effective bed thermal conductivity;
$\dot{q}$ Reaction heat release (W/m³);
h Overall wall heat transfer coefficient;
R Tube radius;
$R_g$ Ideal gas constant;
$\Delta H_{rxn}$ Heat of reaction (J/mol $H_2$);
p Partial pressure;
A Pre-exponential factor (mol/s/m³);
A' Modified pre-exponential factor (W/m³);
E Activation energy;
α Hydrocarbon exponent in rate law;
β $H_2$ exponent in rate law;
$Re_p$ Particle Reynolds number;
$d_p$ Particle diameter;
δ Bed voidage;
L Tube length;
ṁ Gas mass flow rate; and
$C_p$ Gas heat capacity.

In equation 5, "HC" includes all hydrocarbons larger than $CH_4$. The various reaction rates are conservatively assumed to be that of neohexane, because experimental data for this process suggests that neohexane demethylation is faster than demethylation of smaller hydrocarbons. A regression to this data indicates α≈0.17 and β≈2.23. Since the rate is to practically independent of HC concentration, the rate is more of less maximized when the $H_2$ partial pressure is lowest, which occurs at the outlet of the tube. Hence, if the rate at the outlet is used to size the tube, the heat of transfer will be adequate for the remainder of the tube. As such, Equation 1 can be reduced to:

$$\dot{q}(T) = A'\exp\left(-\frac{E_a}{R_g T}\right), \quad \text{Eq. (6)}$$

where A' contains the heat of reaction as well as the partial pressures at the tube outlet. In light of the assumption that the heat of reaction (W/m³) at a given axial coordinate and radial coordinate equals the heat release where the radial coordinate is equal to 0, Equation 6 can be further simplified and Equations 1-2 can be integrated analytically:

$$T_{max} = \frac{A'}{2}\exp\left(-\frac{E_a}{R_g T_{max}}\right)\left(\frac{R^2}{2k} + \frac{R}{h}\right) + T_\infty, \quad \text{Eq. (7)}$$

wherein $T_{max}$ occurs at r=0.

Equation 7 can be solved for R using the quadratic formula, and relates the temperature at the center of the tube to the tube radius, R, and bulk shell-side temperature, $T_\infty$.

Model inputs are set forth in Table 2. The reactor length is chosen to maintain the particle Reynolds number at greater than 100. Bed volume is determined experimentally. Two crucial parameters in Equation 7 are the effective bed thermal conductivity, k, and the overall coefficient of heat transfer, h. Effective bed thermal conductivity depends on the fluid properties, flow rate, inter-particle and/or intra-particle voidage, and particle composition The overall coefficient of heat transfer depends on the film and fouling resistances on both the tube and shell side, as well as the metal conduction resistance, which is assumed negligible in this model. For demethylation of neohexane, h and k are estimated, using the correlations shown in table 3.

TABLE 2

Model inputs excluding heat transfer parameters

| | | Units | Value | Notes |
|---|---|---|---|---|
| Reactor | Length | m | 3.79 | Satisfies |
| | Bed Voidage | | 0.4 | $Re_p > 100$ with lowest possible $\Delta p$ |
| | Bed Volume | m³ | 0.8 | 1.5 WHSV |
| Cooling Water | Temperature | C. | 100 | |
| | Pressure | IPa | 203 | |
| | Velocity | m/s | 5 | |
| Feed | Temperature | C. | 240 | |
| | Pressure | Psig | 150 | |
| | Density | kg/m³ | 8.02 | |
| | Viscosity | cP | 0.06 | |
| | Thermal Conductivity | W/m/K | 0.11 | |
| | Heat Capacity | J/kg/K | 3,168 | |
| Maximum Reaction Rate | $E_a$ | kJ/mol | 127 | |
| | A | mols/s/m³ | 5.16E+13 | $H_2$ pp, $C_{2+}$ pp = 50 psig. |
| | Heat | kJ/mol $H_2$ | 59 | |
| Particle | Diameter | mm | 1.6 | |
| | Porosity | | 0.5 | |
| | Thermal Conductivity | | See Table 3 | |

TABLE 3

Model heat transfer parameters estimated using semi-empirical correlation (Bergman, Theodore L., et al., Fundamentals of heat and mass transfer. John Wiley & Sons, 2011.; Hadley, G. R., International Journal of Heat and Mass Transfer 29.6 (1986): 909-920; Wyatt, J. T., "htpred.for" Fourtran code)

| | | Units | [Internal reference] |
|---|---|---|---|
| Prior Application Thermal Conductivity | Ni | W/m/K | [Internal program] 70 |
| | $SiO_2$ | W/m/K | 1.60 |

TABLE 3-continued

Model heat transfer parameters estimated using semi-empirical correlation (Bergman, Theodore L., et al., Fundamentals of heat and mass transfer. John Wiley & Sons, 2011.; Hadley, G. R., International Journal of Heat and Mass Transfer 29.6 (1986): 909-920; Wyatt, J. T., "htpred.for" Fourtran code)

| | | Units | [Internal reference] |
|---|---|---|---|
| | $Ni/SiO_2$ mixture | W/m/K | 9.56 |
| | Feed gas | W/m/K | 0.11 |
| | $Ni/SiO_2$ catalyst | W/m/K | 1.02 |
| | Stagnant Extrudate bed w/flow | W/m/K | 0.36 |
| | Extrudate bed w/flow | W/m/K | 1.62 |
| Wall heat transfer coefficient | Tubeside film | W/m²/K | 2,040 |
| | Tubeside fouling | W/m²/K | 2,500 |
| | Shellside fouling | W/m²/K | 5,000 |
| | Shellside film | W/m²/K | O(30,000) |
| | Overall | W/m²/K | 880-910 |

Figure 5:
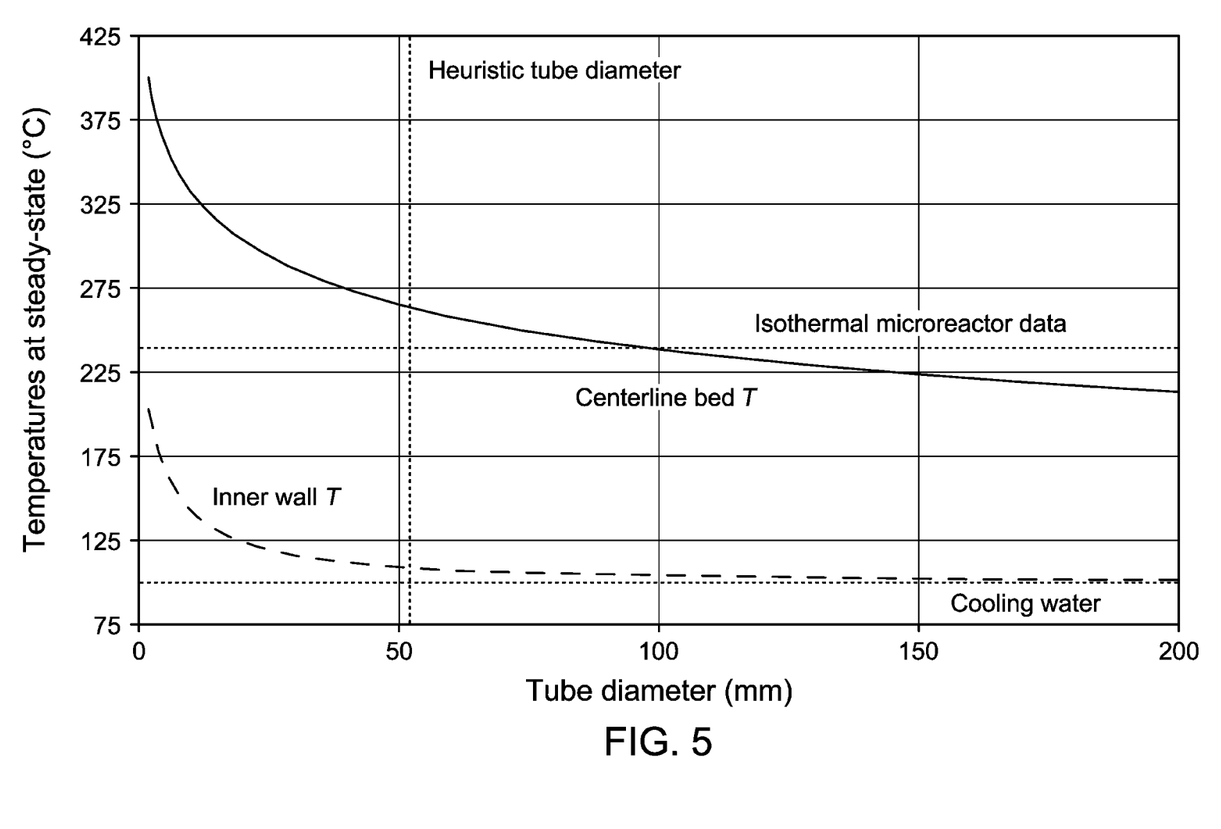
FIG. 5 is a graphical representation of the maximum tube-side centerline temperature that can be kept at a steady state as a function of inner tube diameter.
Figure 6:
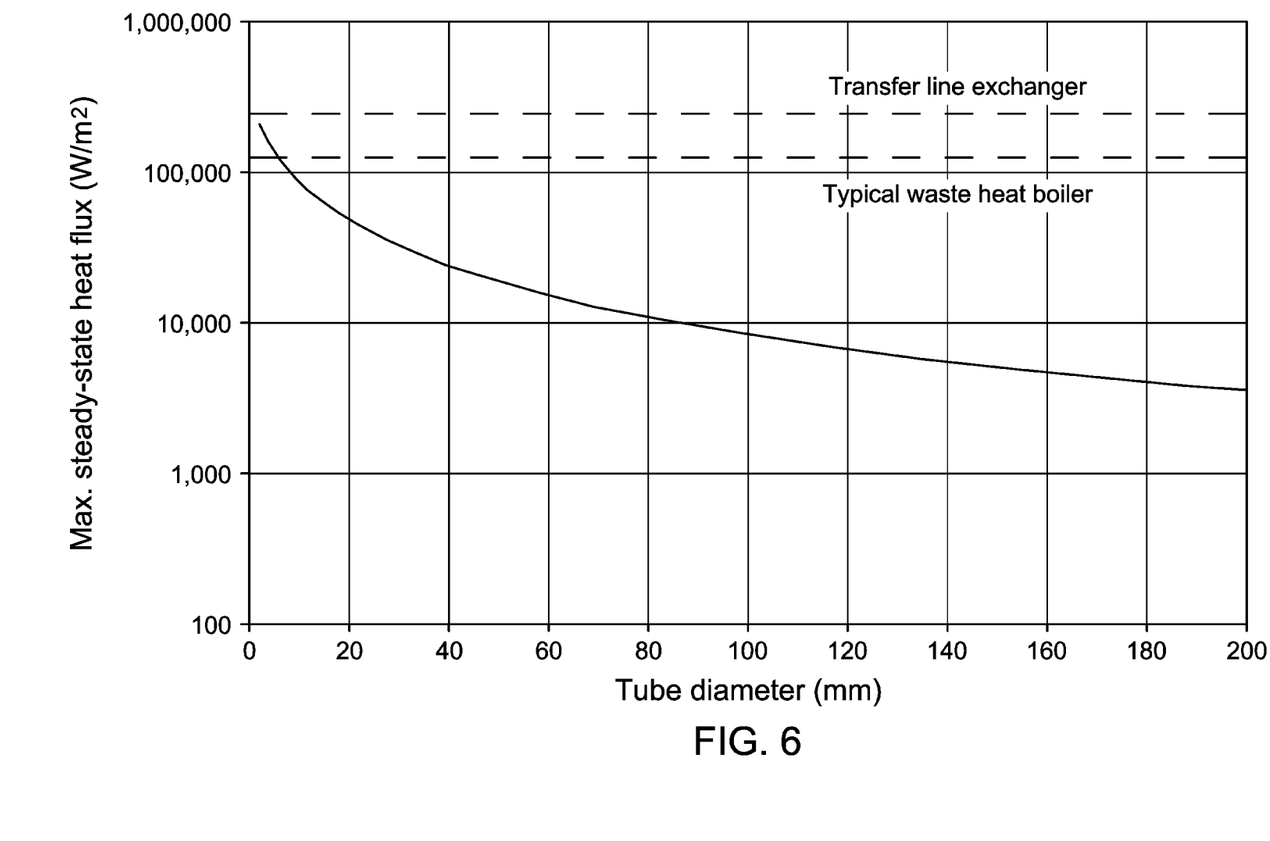
FIG. 6 is a graphical representation of the radial heat flux corresponding to the maximum centerline temperature for steady-state operation of FIG. 5.

The maximum centerline temperature at which a tube can be kept at steady-state was also estimated using the correlations from Table 3, as a function of the inner diameter of the tube. The nominal target temperature is 240° C., corresponding to 52 wt % yield in isothermal microreactor tests. FIG. 5 is a graphical representation of the maximum tube-side centerline temperature that can be kept at a steady state as a function of inner tube diameter. The centerline temperature of a tube could be kept below this threshold with a tube diameter less than 97 mm, as shown in FIG. 5. The corresponding inner wall temperature would be less than 104° C., indicating that there is a significant, unavoidable radial temperature gradient in the bed. FIG. 6 is a graphical representation of the radial heat flux corresponding to the maximum centerline temperature for steady-state operation of FIG. 5. FIGS. 5 and 6 demonstrate robust heat removal capacity at steady state.

Figure 7:
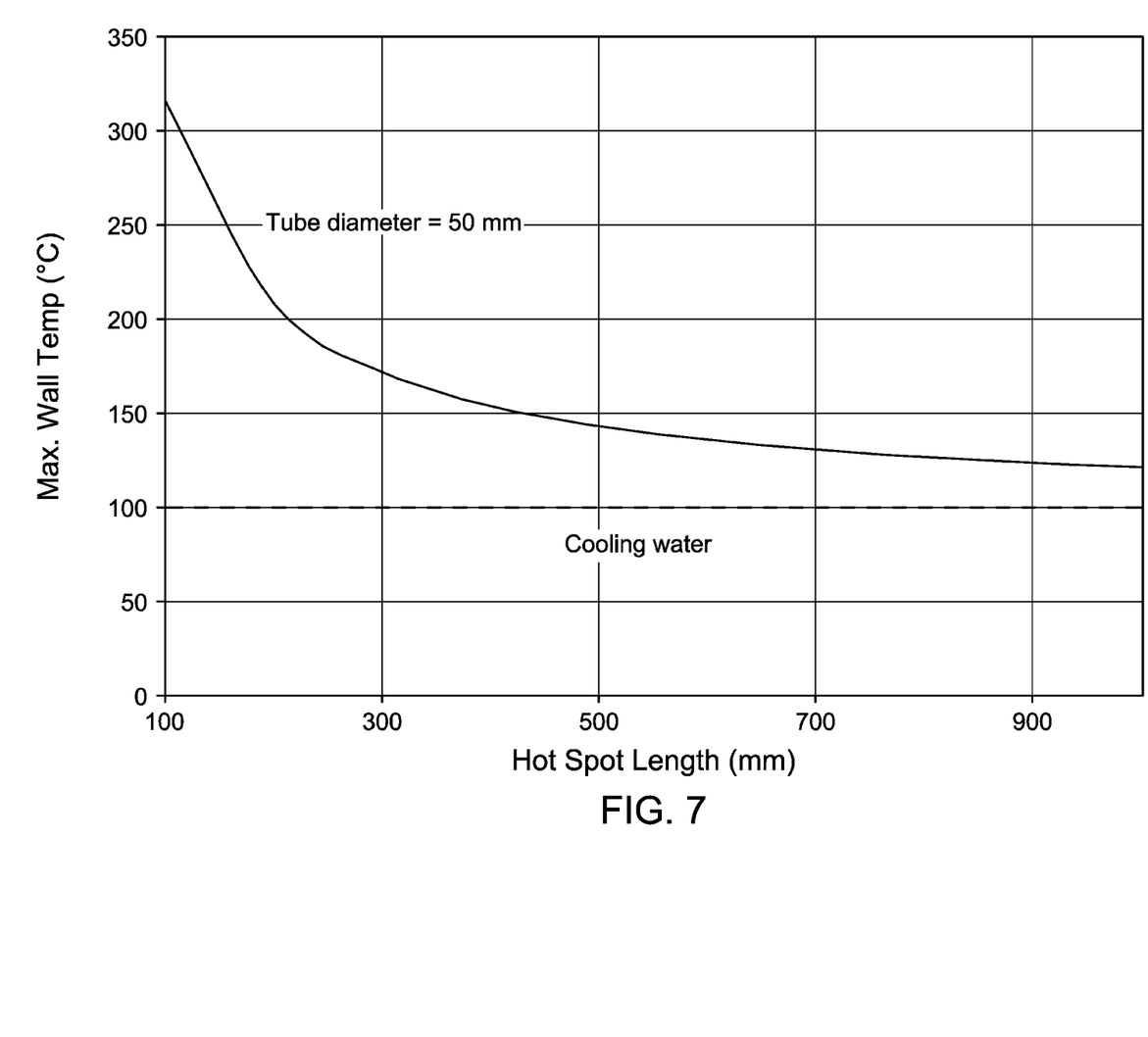
FIG. 7 is a graphical representation of the maximum inner wall temperature reached during the transient ignition/extinction of a hot spot of various lengths for a tube inner diameter of 50 mm.
Figure 8:
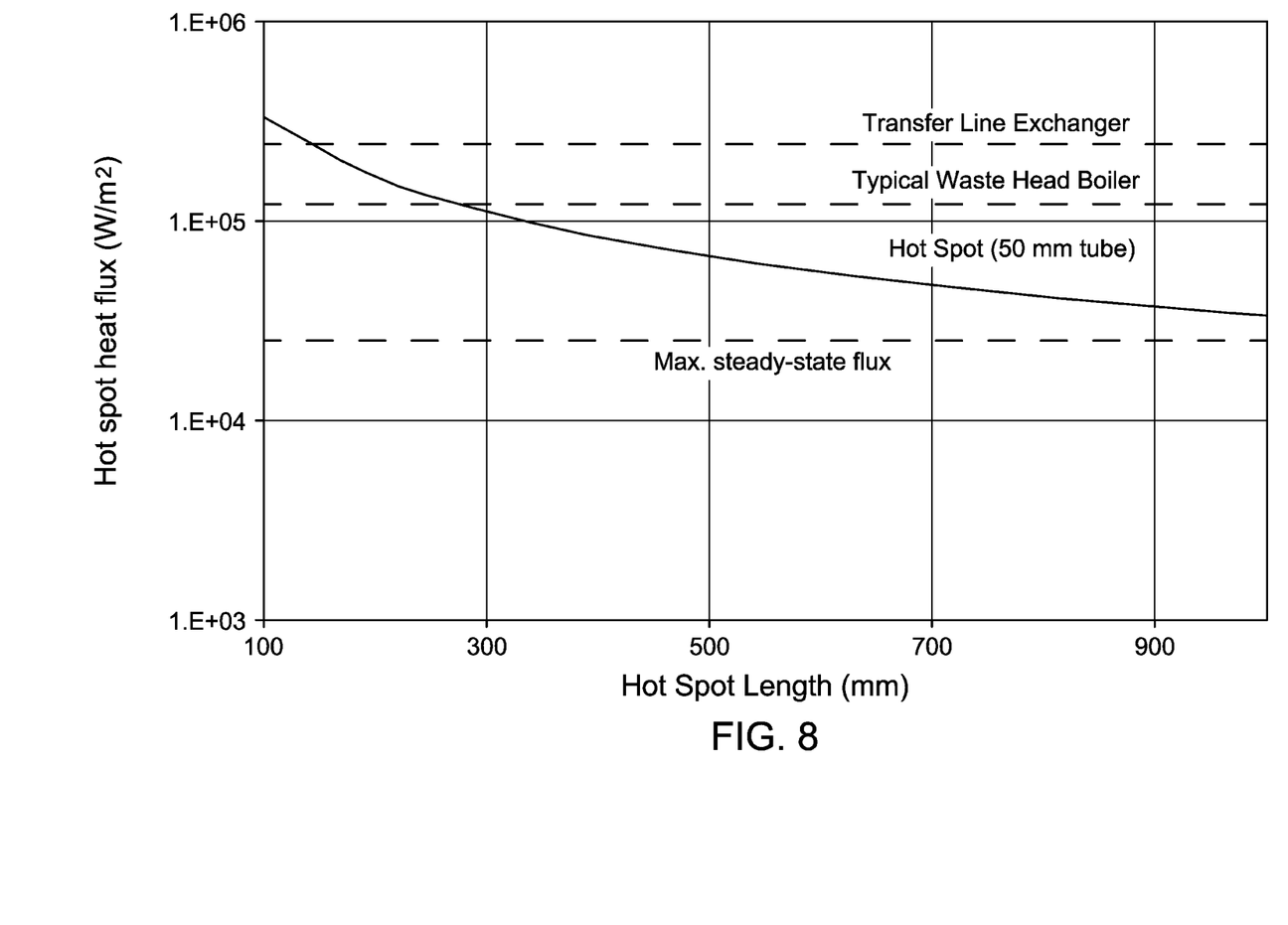
FIG. 8 is a graphical representation of the maximum heat flux reached during the transient ignition/extinction of a hot spot of various lengths for a tube diameter of 50 mm.

Hypothetically, a transient hot spot could still lead to excessive tube wall temperature. In light of this risk the sensitivity of the tube wall temperature to hot spots of different lengths was estimated using Equation 4. The heat release of a hot spot was approximated as the heat release from 100% consumption of the available hydrogen; hence, shorter hot spots have higher heat fluxes in this scenario. The sensitivity of the wall temperature for a 50 mm tube is shown in FIG. 7. For hot spots greater than 200 mm in length (e.g., about 5% of the tube length), the wall temperature is very stable; below 200 mm there is an abrupt change in the slope of the curve. A 200 mm hot spot with 100% $H_2$ consumption is a severe, low-probability event.

These calculations demonstrate that a 50 mm tube can not only meet the process requirements for steady state operation, but can also maintain a safe wall temperature under most runaway conditions. Moreover, a runaway in a tubular fixed bed reactor poses lower potential consequences than in a conventional, adiabatic staged-bed hydrotreater, for example, because one tube failure is insufficient to cause loss of containment across the entire reactor.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process for producing neopentane, the process comprising demethylating a $C_6$-$C_8$ alkane within a shell and tube reactor at a temperature range of from 200 to 500° C., a hydrogen partial pressure of from about 7 psia to about 150 psia, and in the presence of a catalyst comprising a support material comprising Ni and compounds thereof to produce a demethylation product including at least 10 wt % neopentane based on the weight of the demethylation product; wherein the catalyst further comprises at least one member selected from the group consisting of Cu, Au, Ag, Sn, Zn, Re, combinations thereof, compounds thereof, and mixtures of compounds thereof.

2. The process of claim 1, wherein the shell and tube reactor includes a tube having a diameter from 10 mm to 100 mm.

3. The process of claim 1, wherein the diameter is from 40 mm to 60 mm.

4. The process of claim 1, wherein the $C_6$-$C_8$ alkane comprises isooctane.

5. The process of claim 4 further comprising dimerizing isobutylene to produce a dimerization product including diisobutylene and hydrogenating the diisobutylene to produce the isooctane.

6. The process of claim 4 further comprising contacting isobutane with butylenes under alkylation conditions effective to produce an alkylation product including the isooctane.

7. The process of claim 1, wherein the $C_6$-$C_8$ alkane comprises neohexane, neoheptane, or a combination thereof.

8. The process of claim 7 further comprising isomerizing $C_6$-$C_7$ paraffins to produce an isomerization product including the neohexane, neoheptane, or the combination thereof.

9. The process of claim 1, wherein contacting the $C_6$-$C_8$ alkane with the catalyst is carried out at a temperature of about 220° C. to about 300° C.

10. The process of claim 1, wherein contacting the $C_6$-$C_8$ alkane with the catalyst is carried out at a hydrogen to hydrocarbon molar ratio from about 1:1 to about 14:1.

11. The process of claim 1, wherein the catalyst comprises a support material selected from the group consisting of silica, theta-alumina, clay, pentasil, aluminophosphate, carbon, titania, zirconia, and a mixture thereof.

12. The process of claim 1, further comprising separating at least part of the neopentane from the demethylation product.

13. The process of claim 12, wherein separating the neopentane from the demethylation product comprises distilling the demethylation product.

14. The process of claim 12, wherein the demethylation product is separated into fractions comprising (1) a $C_4$- hydrocarbon fraction, (2) a neopentane fraction, and (3) a $C_6$+ hydrocarbon fraction.

15. The process of claim 14, wherein the $C_6$+ hydrocarbon fraction is recycled to the shell and tube reactor.

16. The process of claim 1, wherein the demethylation product comprises about 25 wt % to about 50 wt % neopentane based on the weight of the demethylation product and about zero wt % to about 10 wt % $C_6$+ hydrocarbon components based on the weight of the demethylation product.

* * * * *